US00PP09900P

United States Patent [19]

Plate

[11] Patent Number: Plant 9,900

[45] Date of Patent: May 20, 1997

[54] ANTHURIUM PLANT NAMED MOLLY

[75] Inventor: Renate Plate, Bremen, Germany

[73] Assignee: Wolfgang Bock Pflanzenexport KG, Bremen, Germany

[21] Appl. No.: 559,949

[22] Filed: Nov. 17, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 5,696 3/1986 van der Laarse ..... Plt./88.1

P.P. 9,169 6/1995 Lamb et al. ..... Plt./88.1

*Primary Examiner*—James R. Feyrer

*Attorney, Agent, or Firm*—Foley & Lardner

[57] ABSTRACT

A new and distinct Anthurium plant named 'Molly' particularly characterized by its round or elliptical red spathes each with a red-orange spadix which are held straight above the foliage on sturdy red-orange peduncles. Its leaves are very stiff, leathery, distinctly smooth, and somewhat glossy. The leaf petioles are short, rigid, and straight thereby giving plants of 'Molly' a very compact appearance.

1 Drawing Sheet

The present invention comprises a new and distinct cultivar of Anthurium, botanically known as *Anthurium scherzerianum*, and referred to by the cultivar name 'Molly'.

The new cultivar 'Molly' is a product of a breeding program carried out by the inventor Renate Plate in Bremen, Germany. The cultivar is the result of a cross of selected but unnamed parentage made by the inventor in Bremen, Germany, with the new cultivar being discovered by the inventor from the progeny of the stated cross. Asexual propagation by tissue culture done under the supervision of the inventor in Bremen, Germany was used to increase the number of plants for evaluation and has demonstrated the stability of the combination of characteristics from generation to generation.

The following traits have been repeatedly observed to be characteristics which in combination distinguish 'Molly' from other *Anthurium scherzerianum* cultivars and from the cultivar 'Shazzam', disclosed in U.S. Pat. No. P.P. 9,169.

1. Plants of 'Molly' produce durable cupped elliptical red spathes, with a red-orange spadix. Plants of 'Shazzam', by comparison, produce larger red-orange spathes.

2. Unlike, 'Shazzam', spathes of 'Molly' are held straight above the foliage on sturdy red-orange peduncles.

3. The spathes of 'Molly' are red, with the color darkening with age.

4. The leaves of 'Molly' are very stiff, leathery, moderately thick, distinctly smooth, and somewhat glossy. Leaves of 'Shazzam', by comparison, are more flexible, more textured and less glossy.

5. The leaf petioles of 'Molly' are short, rigid, and straight, giving the plant a very compact appearance when compared to 'Shazzam'.

The following observations, measurements and values describe plants grown in Apopka, Fla. under greenhouse conditions which closely approximate those generally used in horticultural practice.

All color references are measured against The Royal Horticultural Society colour chart. Colors are approximate as color depends on horticultural practices such as light level and fertilization rate, among others, without, however, any change in genotype.

The color photographic drawing comprises a top perspective view of the inflorescence and foliage of a plant of 'Molly' in a 15.2 cm pot. The photograph was taken approximately 10 months after planting a 16-week-old liner obtained by tissue culture and grown under appropriate growing conditions. Colors are as accurate as possible with color illustrations of this type.

Origin: Seedling of selected parentage.

Classification: *Anthurium scherzerianum*, cv. 'Molly'.

Propagation: Asexual production either by tissue culture or division.

Inflorescence: The spathe is tightly rolled aroung the spadix and emerges from the petiole sheath. The spathe is fully open about when the pedicel is fully elongated, approximately 16 cm to 20 cm above the soil surface. The color of the peduncle is greener than but closest to 183 A-178 A, often becoming near red 43 A-B adjacent the base of the spathe.

*Color.*—Upper surface: 42 A, 46 B when mature. Lower surface: 42 A and glossy, 46 C when mature.

*Arrangement.*—The spathes stand up straight on tough wiry peduncles and open above the leaves.

*Shape.*—The spathe is elliptical to round with an obtuse to cordate base and a cuspidate tip that is hooked. It is distinctly cupped when new and often reflexed with age. The spathes are approximately 5.3 cm to 8.0 cm in length, approximately 5.0 cm to 7.4 cm in width, and approximately 1.3 cm in depth just after opening.

*Flowering time.*—Afer approximately 10 months from a 16-week-old liner for an untreated plant having three growing points as illustrated in the color photograph, and depending on season, approximately 3 to 5 inflorescences are present. First flowers (1 to 3) can be expected approximately 4 months after planting a 16-week-old liner.

Reproductive organs:

*Spadix.*—Size: Approximately 3.6 cm to 5.6 cm in length and approximately 6 mm in width. The spadix is straight, often becoming slightly curved with age. Color: The spadix is 33 A-B when new, and 42 A-B when fully emerged. Stamens: Anthers and filaments are minute, and not clearly visible. Pollen: 158 C in color. Pistil: Translucent, 33 D in color, protruding between the staminate flowers, firmly fixed to the main axil. The pistilate flowers extend approximately 0.5 mm beyond the staminate flowers.

General appearance: Under appropriate growing conditions, the mature size of 'Molly' is approximately 16 cm to 20 cm in height and approximately 33 cm to 42 cm in width.

Leaves:

*Form.*—The leaf blade is lanceolate to ovate with an acuminate tip and an obtuse to cordate base. The margins are entire. The midrib is straight over the length of the leaf. The leaf blade is flat or often folded upwaard from the midrib. The leaf margin is straight. The upper leaf surface is somewhat glossy, particularly on newly emerged leaves. The leaves are very stiff, leathery, and moderately thick.

*Size.*—Leaf blades of a mature sized plant are approximately 15.7 cm to 20.2 cm in length and approximately 7.7 cm to 9 cm in width.

*Veins.*—Veins are sunken, and the leaf surface is slightly concave or flat between veins. The midrib protrudes from the upper surface of the leaf for approximately ¾ the length of the leaf. Primary veins border the perimeter of the leaf.

*Petiole.*—The petiole is approximately 7.4 cm to 9.7 cm in height from the base of the petiole to the base of the leaf blade. The petiole is approximately 4.0 mm in diameter just below the geniculum, and is straigh. Two parallel ridges run the length of the upper surface of the petiole.

*Petiole wings.*—Petiole wings are approximately 1.0 cm to 1.2 cm in length and approximately 4.0 mm to 8.0 mm in width at their midpoint. The tips of the petiole wings are rounded. There is approximately 4.5 cm to 7.2 cm between the top of the wing and the base of the geniculum.

*Geniculum.*—The geniculum is approximately 4 mm to 9 mm in length, and approximately 6 mm in diameter. The color is 147 C.

*Lobes.*—The leaf has two rounded lobes which are flush with the petiole/leaf juncture or extend only slightly past the juncture. The distance from the petiole/leaf juncture to the highest point on the lobes is approximately 0.9 cm.

*Color.*—Upper surface: Darker and greener than, but closest to 137 A. Newly emerged leaves have a bronze cast, darker than but closest to 152 A. Lower surface: 146 C-D. Midrib, upper surface: 146 B-C. Midrib, lower surface: 145 C. Petiole: 146 A-B. Petiole wing: 146 A-B, bordered with 187 D.

Roots: Greenish white fleshy roots with fine laterals. The roots are 187 A in color when located above the soil.

General observations: 'Molly' produces durable cupped round or elliptical red spathes with a red-orange spadix. The inflorescences are held straight above the foliage on sturdy, dark red-orange peduncles. The leaves are very stiff, leathery, distinctly smooth, and somewhat glossy. The leaf petioles of 'Molly' are short, rigid and straight, giving the plant a very compact appearance.

It is claimed:

1. A new and distinct cultivar of Anthurium plant named 'Molly', as illustrated and described.

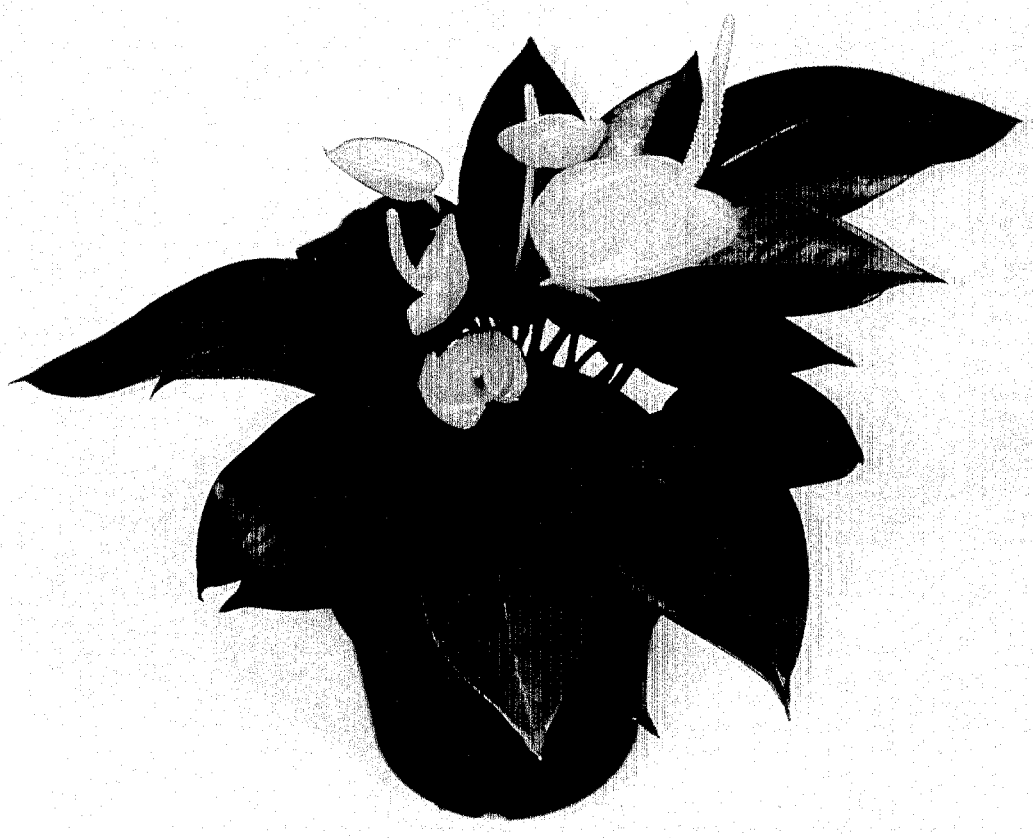

* * * * *